United States Patent [19]

Tackett

[11] Patent Number: 5,789,235
[45] Date of Patent: Aug. 4, 1998

[54] MODIFYING CELL METABOLISM VIA EXTRA-CELLULAR NUCLEASES

[76] Inventor: Scott E. Tackett, 1418 Inglenook, Jefferson City, Mo. 65109

[21] Appl. No.: 562,031

[22] Filed: Nov. 22, 1995

Related U.S. Application Data

[63] Continuation-in-part of Ser. No. 559,149, Jul. 27, 1990, abandoned, which is a continuation-in-part of Ser. No. 029,274, Mar. 23, 1987, abandoned.

[51] Int. Cl.$^6$ .................. C12N 1/38; C12N 1/36
[52] U.S. Cl. .................. 435/244; 435/245; 435/923; 435/947
[58] Field of Search .................. 435/249, 245, 435/255.1, 258.1, 923, 927

[56] References Cited

U.S. PATENT DOCUMENTS 4,376,110  3/1983  David et al. .................. 436/513
4,535,058  8/1985  Weinberg et al. .................. 435/6

OTHER PUBLICATIONS

Belyagva et al., Mikrobiological 46(2): 300–303 (1977).
Bold et al. *The Plant Kingdom*, Prentice–Hall, Englewood Cliffs, NJ. 1987. p. 5.
Brock et al. *Basic Microbiology with Applications*, Prentice–Hall, Englewood Cliffs, NJ. 1986. pp. 154–155.
Stanier et al. *The Microbial World*, Prentice–Hall, Englewood Cliffs, NJ. 1986. pp. 249, 254, 525.
White et al. Construction of linkage maps with DNA markers for human chromosomes, Nature, Jan. 10, 1985, at 101.

*Primary Examiner*—Stephanie W. Zitomer
*Attorney, Agent, or Firm*—Haverstock, Garrett and Roberts

[57] ABSTRACT

This invention involves a method of altering and regulating the gene expression of cells, by means of contacting the cells with a nuclease capable of degrading extra-cellular DNA and/or RNA. The nuclease will degrade the extra-cellular nucleic acids (NA) into nucleotides or oligonucleotides which are too short to have substantial affinity for the chromosomal DNA.

By means of this method, cultures of cells have been created with desirable properties, including greater phenotypic uniformity and higher levels of cell reproduction.

This invention also comprises a culture of cells which has been treated by this method, and cells descended from cells which have been treated according to this method.

3 Claims, No Drawings

MODIFYING CELL METABOLISM VIA EXTRA-CELLULAR NUCLEASES

This application is a continuation-in-part application of U.S. application Ser. No. 07/559,149, filed on Jul. 27, 1990 now abandoned; which is a continuation-in-part application from U.S. application Ser. No. 029,274, filed Mar. 23, 1987 now abandoned.

BACKGROUND OF THE INVENTION

In the double-helical structure of DNA, each strand of DNA consists of a backbone of phosphates alternating with ribose or deoxyribose groups. To each ribose or deoxyribose group is attached a base such as adenine or guanine. The two strands of the double helix are held together by hydrogen bonding, i.e., a hydrogen proton on a base attached to one strand is attracted to an electron pair on a corresponding base on the other strand. This attraction is analogous to two ropes, each of which has a series of magnets tied to it; the ropes can be pulled apart temporarily without tearing each magnet off of its rope, and the ropes can subsequently become re-associated via the attraction of the magnets. The two strands of a DNA molecule must be temporarily associated from each other in order for vital processes (including replication of DNA to allow cell reproduction, as well as transcription of RNA) to take place.

The process whereby two strands of DNA become hydrogen-bonded to each other is referred to as "annealing." Because of the nature of annealing and hydrogen bonding, two strands of DNA that are not exactly complementary can be attracted to each other and will anneal with a substantial degree of stability under normal (e.g., physiological) conditions. In other words, if two strands of DNA inside a cell have similar but not identical sequences of bases, they can be attracted to each other and anneal. This can lead to various types of DNA recombination; see, e.g., Stryer 1981 at page 752 (full citations are listed below, after the examples and before the claims). For example, thymine residues can flex somewhat and form hydrogen bonds with guanine residues, even though thymine usually pairs up with adenine. Under in vitro conditions using Southern or Northern blot hybridization, two strands of DNA or RNA can "hybridize" (become annealed to each other, even though they are not perfectly complementary) with as little as 55% homology (see, e.g., Sano et al, 19&5). Strands with 80% or greater homology can remain attached to each other at temperatures well in excess of 37° C., the normal temperature inside most cells in the human body.

In eukaryotic cells (i.e., cells that have a nuclei, such as higher Protists, including yeast and paramecium cells, plant, or mammalian cells) the chromosomes have substantial numbers of repetitive sequences; see, e.g., Lewin 1985, page 97 et seq. The highly repetitive sequences are often called the "fast components" of the genome, since they reassociate quickly in vitro after they have been denatured (separated) by means such as boiling. These repetitive sequences are now fully understood; it has been hypothesized that they may be involved in genetic recombination or in regulating gene expression.

Eukaryotic genes also have "introns". These are sequences of DNA in the chromosomal genes which are transcribed into sequences of messenger RNA (mRNA) that are excised, in the cytoplasm, from the primary mRNA transcript before the edited mRNA is translated into protein; see, e.g., Lewin 1985, page 81 and 312, and Stryer 1981, page 702. Introns (as well as edited mRNA) are eventually digested (i.e., broken down into their building blocks which are called nucleotides, each of which contains a phosphate group, a ribose ring, and a base) in the cytoplasm, primarily by enzymes called "nucleases". However, there are reasons to presume that at least some introns either diffuse back into the nucleus or are actively transported into it, before they are digested into nucleotides. This is evidenced by the fact that viral nucleic acids, which must pass through the cytoplasm of a cell, quite frequently reach the nuclei of eukaryotic cells.

A nuclease which preferentially digests RNA (i.e., it digests RNA without digesting DNA at a comparable rate) is called an RNase (also capitalized as RNase); conversely, a nuclease which digests DNA more rapidly than RNA is called a DNase or DNAse. Non-specific nucleases which digest either DNA or RNA at roughly comparable rates are simply called nucleases. As used herein, the term "nuclease" includes all three categories of enzymes.

The terms "DNA" "RNA" and "nucleic acids" refer to polynucleotides, and to oligonucleotide strands having a sufficient number of bases to anneal with substantial avidity to a strand of DNA or RNA; those terms do not apply to single nucleotides, dinucleotides, or other strands too short to bind with any substantial avidity to a long strand of DNA or RNA having a complementary sequence. Avidity refers not just to the attraction between hydrogen-bonding molecules, but also to their ability to remain coupled together over a prolonged span of time.

As used herein, "non-chromosomal nucleic acids" refers to nucleic acid strands which are inside a living cell, but which are not covalently bound to chromosomes (i.e., they are not part of either primary strand in a chromosome; however, they might be hydrogen-bonded to one of the primary strands). Non-chromosomal nucleic acids include mRNA, transfer RNA, ribosomal RNA, and introns which have been removed from mRNA. It also includes any other strands of DNA or RNA which are in a living cell but which are not incorporated into a chromosome; this includes DNA or RNA from a virus which has infected a cell, as well as oligonucleotides or polynucleotides generated during digestion or as a result of cell death and lysis, which have been taken up by cells. Once inside the cell, the strands usually are digested further, into single nucleotides that function as metabolites for the cell.

It has been known since at least 1935 that certain types of restricted diets promote a longer life span in laboratory animals compared to animals fed an ad libitum diet (i.e., a diet where the animals can eat all they care to eat); see McCay et al 1935. In the 1970's, it was established that dietary restrictions increase average lifespans and reduce the rate at which aging occurs (see the chapter by G. A. Sacher in Finch and Hayflick 1977). In the past few years, it has been discovered that dietary restrictions can significantly delay the onset of various age-associated degenerative diseases, including cancer, arthritis, renal disease, and osteoporosis (see Masoro 1985 and Holehan and Merry 1986). However, despite a large amount of research being done in the field of aging and gerontology, there is no accepted explanation for those facts, and there have been few if any proposals for converting those findings into methods for prolonging life or delaying age-related disease except for recommendations that people should eat less than they want to eat.

To the best of the Applicant's knowledge, no one has demonstrated a practical method for-modifying the entry of non-chromosomal nucleic acids into eukaryotic cells, spe-

3 cifically higher Protists cells, as a method of controlling gene expression. Similarly, no one has previously suggested that oligonucleotides and polynucleotides which are taken into cells as nutrients might interfere with proper functioning of the genes.

SUMMARY OF THE INVENTION

This invention involves a method of altering the gene expression of higher Protists cells, such as cells found in the Mycetae and Protists kingdoms including cells in the Protozoa and Ascomycetes subdivisions, in an inheritable manner, by means of contacting the cells with an exogenous nuclease (an enzyme capable of degrading extra-cellular DNA and/or RNA). The nuclease will degrade extra-cellular nucleic acids into nucleotides or oligonucleotides which are too short to have substantial avidity for chromosomal DNA.

By means of this method, cultures of cells have been created with desirable properties, including greater phenotypic uniformity and higher levels of cell reproduction.

This invention also comprises a culture of cells which has been treated by this method, and cells descended from cells which have been treated according to this method.

DESCRIPTION OF THE PREFERRED EMBODIMENTS

This invention involves a method of treating eukaryotic cells, including mammalian cells, but more specifically higher Protists cells selected from the Kingdoms Protista and Mycetae. The Protista kingdom includes subdivision Protozoa and genus species selected from the group consisting of *Paramecium caudatum*, *Paramecium aurelia*, and *Paramecium tetraurelia*. The Mycetae kingdom includes subdivision Ascomycetes and genus species *Candida lipolytica*. Thus, this invention will specifically treat yeast and paramecium cells. The invention comprises the step of treating the higher Protists cells with an exogenous nuclease added to an extra-cellular fluid that is in fluid communication with the cells, wherein the exogenous nuclease remains in the extra-cellular fluid under suitable conditions and for an adequate period of time to allow the exogenous nuclease to digest extra-cellular oligonucleotides and polynucleotides in the fluid. The exogenous nuclease will digest extra-cellular nucleic acids into nucleotides or oligonucleotides which are too short to bind with substantial avidity to the chromosomal DNA. This effectively alters the diffusion and uptake of extracellular oligonucleotides and polynucleotides into the cells, thereby altering the concentration and distribution of oligonucleotides and polynucleotides inside the cells which are non-covalently bound to the chromosomes of the cells. This type of treatment has been shown to cause inheritable phenotypic alterations which are expressed by progeny cells after more than three generations.

The method of this invention does not necessarily lead to alteration of the DNA in the main strands of the chromosomal double helices. Instead, this method can be roughly summarized by the phrase, "cleaning the chromosomes." The nuclease treatment of this invention alters the distribution of oligonucleotides and polynucleotides in the extracellular fluid, which are generated by various processes such as digestion, cell death and lysis, etc. Extra-cellular oligonucleotides and polynucleotides can diffuse or be actively transported into cells, since they normally serve as nutrients once they enter a cell. However, the inventor has discovered that such oligonucleotides and polynucleotides, if they remain in relatively long strands, apparently can diffuse or be transported through the cytoplasm and into the nuclei of higher Protists cells. After they reach the nuclei, the exogenous strands can anneal to single strands of DNA that become exposed when a segment of DNA temporarily opens up to allow for transcription, replication, or other processes.

When an exogenous polynucleotide anneals to an exposed single strand of chromosomal DNA, the semi-complementary polynucleotide binds to the chromosomal strand less tightly than the fully-complementary chromosomal strand would bind, but still tightly enough to remain attached for some period of time. In a sense, the exogenous polynucleotide creates a "pseudo-strand" that binds to and entangles one of the strands of the chromosomal DNA, preventing that strand from returning to the double helical configuration with its fully complementary true chromosomal strand. In that manner, the pseudo-strand interferes with the proper functioning of any genes that are contained within or affected by the region of DNA that is entangled by the exogenous polynucleotide.

That problem remains unless and until the exogenous polynucleotide is removed somehow; however, the process of removal might never happen in a particular cell. A gene might remain entangled and encumbered by the exogenous polynucleotide until the cell or the organism that contains the cell eventually dies.

Alternately, an exogenous polynucleotide might be substituted for the original DNA sequence. This process would involve several steps, including (1) the annealing of an exogenous strand to an exposed semi-complementary single strand of chromosomal DNA, followed by (2) the mistaken excision of the proper strand by a chromosomal repair mechanism which cannot properly distinguish between the proper strand and the pseudo-strand, followed by (3) the generation of a second strand of DNA which is incorporated within the chromosome, to match the exogenous strand. In this process, the exogenous strand would displace and eliminate the proper gene.

Even if an exogenous pseudo-strand is recognized as exogenous and is removed and digested into nucleotides by some chromosomal repair mechanism, the proper expression of the affected gene(s) will be inhibited for as long as it takes for the repair mechanism to recognize and get rid of the exogenous strand.

The subject invention centers around the following discovery: by digesting exogenous oligonucleotides and polynucleotides while they are in the extra-cellular fluid, before they enter the cells of the higher Protists, it is possible to alter the presence and distribution of exogenous oligonucleotides and polynucleotides inside the cells. That process, in turn, alters the rate or quantity of non-covalent binding of exogenous oligonucleotides and polynucleotides to the chromosomes of cells. The process is in essence a two part process whereby the exogenous nuclease degrades extracellular nucleotides and oligonucleotides, which leads to a change in equilibrium between the extra-cellular nucleotides and the intra-cellular nucleotides/oligonucleotides, resulting in a passage of nucleotides from the cytoplasm of the cell to the extra-cellular fluid. Once this occurs there is a change in equilibrium between the non-chromosomal nucleotides, attached to the chromosome in the nucleus, and the nucleotides present in the cell's cytoplasm, which results in the passage of the non-chromosomal DNA from the nucleus, where it is hydrogen bonded to the chromosome, to the cytoplasm of the cell. Therefore, treatment with exogenous nucleases causes measurable and inheritable phenotypic alterations in the cells. By "cleaning the chromosomes" (or, more precisely, by preventing them from becoming entangled by unwanted exogenous polynucleotides), proper gene expression is protected and enhanced.

As used herein, the term "nuclease" refers to an enzyme capable of degrading extra-cellular DNA and/or RNA. An "exogenous" nuclease refers to a nuclease originally produced by cells other than the cells being contacted, and to nucleases produced by artificial means such as peptide synthesis or chemical alteration of a different enzyme.

The phrase, "altering the gene expression" refers to changes which are observable using available methodology. Such changes may involve phenotypic alterations such as cell or culture morphology, pH of cell metabolites or cell culture fluids, expression of one or more observable polypeptides, etc., or they may involve genotypic alterations observable by means of DNA or RNA hybridization using Southern or Northern blots or similar methods.

As used herein, the phrase "in an inheritable manner" refers to genotypic or phenotypic alterations that remain in, or are expressed by, a genome after more than three generations. Culturing cells for at least three generations will eliminate transient alterations due to chemical interactions in the original culture medium. However, this does not require that the alterations be indefinite in duration, as would be caused by inserting a new gene into a chromosome and covalently lighting both ends of both DNA strands of the gene to the DNA in the chromosome. A transient alteration is sufficient, if it is inherited and expressed by more than three generations of cells.

The phrase, "contacting the cells with an exogenous nuclease for the purpose of digesting extra-cellular nucleic acids" does not include cell and nuclease contacts which are merely incidental to other intended purposes. For example, whenever a cell dies, it releases nucleases which had been digesting mRNA into nucleotides within that cell's own cytoplasm. Such release is merely incidental, and is not included within the cited phrase. Similarly, scientists have contacted various types of cells with nucleases and have measured certain effects which are highly transient rather than inherited; for example, Belyaeva et al 1977 showed that nucleases from *Serratia marcescens* caused a transient increase in the replication of *Candida tropicalis*; that increase lasted only for three hours, and there was no proposed explanation for it. Several years later, Belyaeva's coworkers (Kupriyanova et al 1982) suggested that the mechanism by which the nucleases increased yeast replication involved the nicking of chromosomal DNA. In their hypothesis, multiple breaks in the chromosomal strands provided the replication system with multiple sites at which the process of replication could commence. Kupriyanova et al further stated that RNase had no effect on cell division rates; that was consistent with their theory and observations. However, despite that teaching, the Applicant generated inheritable phenotypic differences by treating cells with RNase.

Yeast Experiments

Several experiments were performed on fungi such as yeast and more specifically, *Candida lipolytica*. As described in Example 1, cultures of yeast cells were incubated with RNase, DNase, or both for two months at room temperature. Yeast from each tube was streaked onto an agar plate. A week later, nine presumably clonal colonies were taken from each of the four plates; each cell sample was inoculated into a tube containing fresh broth (one culture per tube, 36 tubes total). A week later, each tube was used to inoculate 9 additional tubes containing 5 ml broth (one culture per tube), using a sterilized loop to transfer cells from one tube to another. The yeast cells were cultured for a week. Since their doubling time can be as short as 30 minutes when grown in optimal conditions, yeast cells grown in a fixed and limited amount of medium without adding additional nutrient or removing metabolites are assumed to grow to their maximal density within a few days. Therefore, culturing them for a prolonged period such as a week will minimize any differences due to varying numbers of cells in the initial inoculant and will decrease any statistical variations associated with such differences. After a week of culturing the yeast in 5 ml of nutrient medium, the pH of each tube was measured. The data was statistically analyzed to provide the following data for the total sum of the squares variance (TSSV) and F values:

TABLE 1

| Treatment | TSSV | F value |
|---|---|---|
| Untreated (control) | 0.9464 | 1.99 |
| DNase | 0.9716 | 2.07 |
| RNase | 1.1817 | 8.54 |
| DNase and RNase | 0.7272 | 1.87 |

The F value is defined as the species or treatment mean square, divided by the error mean square (see Woolf 1968 at pages 91–93). In practical terms, F values are used to determine whether a variation between two or more different populations is statistically significant at some arbitrary level, such as the 95% or 99%. By contrast, statistical measures such as standard deviation are useful for determining how a single data point relates to a probability distribution.

If the degrees of freedom are $DF_1=8$ and $DF_2=64$, an F value higher than about 3 has less than a 1% chance of occurring randomly (Table IVb, page 331 in Woolf 1968). Since the F value for the RNase treatment jumped to 8.54, it was clearly statistically significant. The low F value was also statistically significant because it meant that the variance in pH between the yeast cell populations was very low, which meant that the metabolism of the yeast cell populations was quite similar. This can be interpreted to mean that very little genotypic or phenotypic variability existed from one yeast population to the next, and that the progeny were quite similar. Thus, the nucleases cleaned the chromosomes preventing the non-chromosomal DNA from affecting the chromosomes and resulting in progeny cells with nearly identical phenotypes, thus there appeared to be more uniformity in the phenotypes then what would normally exist.

Those anomalous results suggested that the RNase treatment was imposing an important type of stress on the cells, which the Applicant could not identify or explain at the time. In particular, the similar values for the untreated and DNase treated cultures were closer than anticipated, while the TSSV and F value data for the RNase-treated culture was substantially higher. While searching for possible causes, the Applicant discovered an article which revealed that *Candida lipolytica* secretes an endogenous RNase (Ogrydziak et 21, 1977). In view of that fact, the results suggested the following:

a. The ratio of extracellular DNA to extra-cellular RNA, which presumably affects the intracellular non-chromosomal DNA/RNA ratio, appears to be important. *Candida lipolytica* secretes RNase and grows well at the extra-cellular DNA/RNA ratios created by that RNase. When an additional high quantity of RNase is added, the DNA/RNA ratio is altered, which places the cells under stress as indicated by the higher phenotypic variability. This phenotypic variability apparently is inheritable, as evidenced by the fact that the pH measurements were taken on cultures grown for three weeks after the nuclease treatment was terminated.

b. When only DNase was used to treat the cells, instead of RNase, the DNA/RNA ratio was not altered as much, since both RNA and DNA were being digested outside the cell. Therefore, the variability of the culture increased somewhat, but not as much as with the RNase treatment.

c. A single treatment with both DNase and RNase caused a reduction in the total variability of the culture. Under at least some lab conditions, reducing the variability of a culture is highly desirable.

Several sets of experiments were planned and carried out to test those hypotheses, including follow-up experiments using subsequent RNase treatment on the same cell cultures. Ten weeks after the initial treatment, a culture from each group treated as described in example 1 was transferred to an agar plate and grown for a week. Clonal colonies were selected and a few cells from each colony were transferred into 5 ml of liquid broth containing RNase. The cells were incubated with the RNase for three weeks. Yeast from each tube was streaked onto an agar plate. A week later, nine cultures were taken from each of the four plates and inoculated into 36 tubes containing fresh broth (one culture per tube). A week later, each tube was used to inoculate 9 additional tubes containing 5 ml broth (one culture per tube). They were incubated for another week before the pH readings were taken. These tests are described in more detail in Example 2.

It should be noted that the cells were cultured for three weeks after the exonuclease treatment stopped, before the pH measurements were taken. During that period of time, they were transferred three times to fresh nutrient. Therefore, any nongenetic factors would have been diluted out.

TABLE 2

| First Treatment | Second Treatment | TSSV | F value |
| --- | --- | --- | --- |
| Untreated | RNase | 0.5666 | 13.63 |
| DNase | RNase | 0.2862 | 5.57 |
| RNase | RNase | 0.9950 | 46.59 |
| DNase & RNase | RNase | 0.2546 | 4.22 |

The variations induced by the exonuclease treatment are highly significant (at confidence levels greater than 99%). In addition, the variations induced by the treatment are inherited, as evidenced by the fact that the differing phenotypic traits were expressed after numerous generations, after the descendant cells were transferred multiple times to different culture media which did not contain exonuclease.

These results, in connection with the fact that *Candida lipolytica* secretes its own RNase, are consistent with the results of the first set of tests. They indicate that treatment of a cell culture with DNase (which works in conjunction with the endogenous RNase), or with both DNase and RNase, reduce the variability of the culture. By contrast, the treatment with RNase alone created a greater variability.

In a third set of experiments, yeast cells that had been treated with RNase as described in example 1 were subsequently subjected to one of four types of treatment. Ten weeks after the initial RNase treatment, cells were transferred to an agar plate and grown for a week. Clonal colonies were selected and a few cells from each colony were transferred into four tubes (one colony per tube), each containing liquid broth with one of the four treatments (control; DNase; RNase; DNase and RNase). The cells were incubated for three weeks, and yeast from each tube was streaked onto an agar plate. A week later, nine cultures were taken from each of the four plates and inoculated into 36 tubes containing fresh broth (one culture per tube). A week later each tube was used to inoculate 9 additional tubes containing broth (one culture per tube). They were incubated for another week before the pH readings were taken. The resulting data are provided in Table 3.

TABLE 3

| First Treatment | Second Treatment | TSSV | F value |
| --- | --- | --- | --- |
| RNase | Untreated | 0.2870 | 2.67 |
| RNase | DNase | 0.2758 | 2.41 |
| RNase | RNase | 0.9950 | 46.59 |
| RNase | DNase & RNase | 0.2656 | 14.60 |

All of these results support the conclusion that digestion of extracellular polynucleotides by extracellular nucleases can alter the intracellular concentration and distribution of polynucleotides to an extent that causes an inheritable phenotypic change in progeny cells.

Paramecium Experiments

Additional experiments (described in Examples 5 and 6) were performed on paramecium, because paramecium have a well documented aging cycle similar in some respects to the aging cycles in humans and other higher animals (see, e.g., Rodermel et al 1977 and Hayflick 1975). Treatments which increase the rate of reproduction of paramecium are presumed to have a beneficial effect on the cells.

Cultures of paramecium were inoculated into tubes containing 0.5% DNase or 0.5% albumin (control) in protozoan broth. After a week, 30 cells were isolated from each tube. Each cell was placed in a separate tube containing fresh broth, and after 24 hours, the number of paramecium cells in each tube was counted and recorded. The mean number of DNase-treated paramecium cells was slightly higher than the albumin-treated cells; however, the difference was not statistically significant. Cells treated with 1% RNase showed a slight decrease in division rate during the first 24 hours, then a slight increase in division rate, which became statistically significant after about 2 weeks.

A series of additional tests on paramecia were conducted using a series of enzyme treatments, as follows:

TRIAL A: Cells were treated with 1% DNase. Once each hour for the next four hours, an additional 1% DNase was added.

TRIAL B: 4% RNase was added to the solution a total of 9 times, once every 30 minutes.

TRIAL C: 4% RNase was added to the solution 5 times, once every hour.

TRIAL D: Cells were treated initially with 1.5% DNase and 1% RNase. Every 30 minutes after that, 1% RNase was added, a total of 8 times.

TRIAL E: 1% DNase and 1% RNase were added to the solution 5 times, once each hour.

TRIAL F (CONTROL): Cells were grown in broth with salt, buffer, and bacteria, with no nuclease.

The number of cells at the end of the 24 hour period in all nuclease-treated trials listed above were significantly less than the number of control cells. Therefore, the Applicant modified the concentrations and time variables and substantially increased cell division, as follows:

TRIAL G: 0.5% DNase was added to the solution 3 times, once every 2 hours.

TRIAL H: 2% RNase was added to the solution 3 times, once every 2 hours.

TRIAL I: Cells were treated initially with 1.5% DNase and 1% RNase, then 1% RNase was added two more times, once every 2 hours.

TRIAL J: 0.5% DNase and 0.5% RNase were added to the solution 3 times, once every 2 hours.

All cells treated as described above had higher division rates, tested after one week. The results are shown in Table 4. The increase in the division rate was statistically significant at the 99% level in Trials G and J. Trial I was significant at the 95% level, and Trial H was significant at the 90% level.

TABLE 4

| Treatment | # cells (mean) | Level of siqnif. |
| --- | --- | --- |
| Control | 3.65 | — |
| G: 0.5% DNase, 3× | 5.0 | 99% |
| H: 2% RNase, 3× | 4.65 | 90% |
| I: DNase & RNase/ RNase/RNase | 4.9 | 95% |
| J: DNase & RNase, 3× | 5.5 | 99% |

Additional Comments

As indicated by the results above, two types of beneficial effects have been identified in the experiments completed to date:

1. reductions in culture variability. This can be very valuable, since certainty, predictability, and repeatability are extremely useful in both research and industrial microbiology.
2. increases in the cell division rate, and presumably the vitality, of paramecium.

Instead of being gene-specific genetic engineering, this treatment is analogous to a shot-gun approach. The treatment can be used on any culture of eukaryotic cells, and the actual effects can be determined by analyzing the treated cells. For example, if microbiologists wish to increase the homogeneity of a culture of cells for research or industrial fermentation purposes, they can use the method of this invention to treat numerous cultures of cells of the selected species, analyze each treated culture to determine its level of homogeneity (by measuring variables such as pH, the quantity of a certain molecule produced by sub-cultures, or net metabolic activity of the entire culture) and select one or more treated cultures having an increased level of homogeneity and uniformity for further use.

Nucleases suitable for use in this invention may be purchased commercially, or purified using published techniques. Some nucleases degrade DNA but not RNA, others degrade RNA but not DNA, and some degrade both DNA and RNA. For any specific use, the following variables can be assessed using no more than routine experimentation:

1. the preferred type of nucleases or the preferred mixture of two or more nucleases. The ratio of DNA to RNA digested outside the target cells has been shown to be important, as discussed above. Routine tests can be performed to determine suitable DNase/RNase ratios for any specific use.
2. the concentration of cells and nuclease(s) to be used in the initial treatment;
3. the timing and concentration of subsequent treatments;
4. the duration of each treatment; and
5. the optimal age of the culture and preferred reaction conditions such as salt and buffer content, temperature, stirring, etc.

This invention also comprises a culture of cells which has been treated by this method, and cells descended from cells which have been treated according to this method.

Those skilled in the art will recognize, or may determine using no more than routine experimentation, numerous equivalents to the specific embodiments discussed herein. Such equivalents are within the scope of the claims.

EXAMPLES

Example 1

EFFECTS OF ADDING NUCLEASE TO YEAST CULTURES

The yeast used in the experiments described herein is from the species *Candida lipolytica*, which also referred to in the literature as *Saccharomycopsis lipolytica* if it undergoes certain types of sexual recombination (see Yarrow 1972). The specific strain used is designated as the CX 39-74C ural strain, described in Ogrydziak et al 1978. It is an auxotrophic strain generated by UV radiation and cannot synthesize uracil. This strain was obtained from Dr. John Bassel who was at the Donner Laboratory at the University of California at Berkeley.

Cultures of yeasts cells were inoculated from an agar plate into 4 tubes containing 10 microliters (ul) 1M magnesium chloride, 10 ul 1M Tris buffer, pH 7.6, and the following enzymes:

Tube R: 20 ul of RNase

Tube D: 20 ul of DNase

Tube DR: 20 ul of each enzyme

Tube C (control): no enzymes.

Each tube also contained enough sterile distilled water to make 1 ml of solution before the yeast was added. The RNase was prepared by dissolving RNase A (Sigma Chemical Co., St. Louis, Mo.) at 10 mg/ml in 10 mM Tris-HCl, pH 7.5, 15 mM NaCl, heating at 100 degrees C. for 15 minutes, and slowly cooling to room temperature. The DNase was prepared by dissolving 2 mg/ml of DNase 1 (Sigma Chemical Co.) in sterile 0.02M sodium acetate, pH 5.2 with acetic acid, and adding an equal volume of autoclaved glycerol.

After two months at room temperature, yeast from each tube was streaked onto an agar plate. One week later, nine cultures were taken from each plate and inoculated into tubes containing 5 ml of PRD broth. All 36 tubes were assigned numbers by a neutral party, and were subsequently measured with no knowledge of which batch they came from. A week later each tube was used to inoculate 9 additional tubes containing 5 ml PRD broth each, in groups of 3 tubes in 5 minute time blocks. A week later, the pH of each tube was measured, in the same sequence as the inoculation using 5 minute time blocks. The data were given to the neutral party, who then revealed the tube numbering system. The untreated control cultures had a mean pH of 7.05, a total sum of the squares variance (TSSV) of 0.9464, and an F value of 1.99. The cultures treated with DNase only had a mean pH of 7.02, a TSSV of 0.9716, and an F value of 2.07. The cultures treated with RNase only had a mean pH of 7.06, a TSSV of 1.187, and an F value of 8.54. The culture treated with both DNase and RNase had a mean pH of 7.03, a TSSV of 0.7272, and an F value of 1.87.

These results were not entirely expected. While searching for possible causes, the Applicant; discovered an article which revealed that *Candida lipolytica* secretes at least one protease (Tobe et al, 1975) and at least one RNase (Ogrydziak et al, 1977). In view of that fact, the results made sense and suggest the following:

a. The ratio of extra-cellular DNA to extra-cellular RNA, which presumably affects the intra-cellular, non-chromosomal DNA/RNA ratio, is important. *Candida lipolytica* has evolved its own supply of RNase and grows well at the extra-cellular DNA/RNA ratios created by that RNase. When an additional high quantity of RNase is added, the DNA/RNA ratio is drastically altered which places the cells under stress, as indicated by the higher phenotypic variability. This phenotypic variability apparently is inheritable, as evidenced by the fact that the pH measurements were taken on cultures grown for three weeks after the nuclease treatment was terminated.

b. When only DNase was used to treat the cells, instead of RNase, the DNA/RNA ratio was not altered as much, since both RNA and DNA were being digested outside the cell. Therefore, the variability of the culture increased somewhat, but not as much as with the RNase treatment.

c. A single treatment with both DNase and RNase caused a reduction in the total variability of the culture. Under at least some lab conditions, reducing the variability of the culture is a highly desirable effect.

Example 2

EFFECTS OF SUBSEQUENT NUCLEASE TREATMENTS ON YEAST

Yeast cultures were treated with DNase, RNase, both, or nothing (control) as described in Example 1. After ten weeks, a culture from each group was transferred to an agar plate, and grown for one week. A culture was taken from each agar plate, inoculated into a tube containing RNase and various salt and buffer solutions described in Example 1, and incubated at room temperature for three weeks. Yeast from each tube were streaked onto agar. One week later, nine colonies from each plate were inoculated into 5 ml of PRD broth. The 36 tubes were numbered by a neutral patty. One week later, each tube was used to inoculate 9 tubes of 5 ml PDR broth. One week later, the pH of the tubes was analyzed. The results are shown in Table 1.

The culture which was initially not treated (the control) had a TSSV of 0.5666 and an F value of 13.63 after the second step RNase treatment. The culture which was initially treated with DNase had both a lower TSSV (0.2862) and a lower F value (5.57). The culture which was initially treated with both DNase and RNase also had a lower TSSV (0.2546) and a lower F value (4.22). By contrast, the culture which was initially treated with only RNase, and subsequently treated with only RNase, had a much higher TSSV (0.995) and an extremely high F value (46.59).

These results, in connection with the fact that *Candida lipolytica* secretes its own RNase, are consistent with the results of Example 1. They indicate that treatment of a cell culture with DNase (which works in conjunction with the endogenous RNase), or with both DNase and RNase, reduce the variability and presumably the stress on the culture. By contrast, the treatment with RNase alone imposed greater stress on the culture and created a greater variability.

Example 3

EFFECTS OF SUBSEQUENT NUCLEASE TREATMENTS ON YEAST TREATED WITH RNASE

Yeast cultures were treated with RNase as described in Example 1. After ten weeks, a culture from each group was transferred to an agar plate, and grown for one week. Four cultures were taken from the agar plate, inoculated into four tubes. Each tube contained one of the solutions described in Example 1. All four tubes were incubated at room temperature for three weeks. Yeast from each tube were streaked onto agar. One week later, nine colonies from each plate were inoculated into 5 ml of PRD broth. The 36 tubes were numbered by a neutral party. One week later, each tube was used to inoculate 9 tubes of 5 ml PDR broth. One week later, the pH of the tubes was analyzed. The culture which received no second treatment (the control) had a TSSV of 0.287 and an F value of 2.67. The culture which received a second treatment with DNase had a TSSV of 0.2758 and an F value of 2.41. The culture which was treated twice with only RNase had a TSSV of 0.995 and an F value of 46.59. The culture which received a second treatment with both DNase and RNase had a TSSV of 0.2656 and an F value of 14.6.

Example 4

EFFECTS OF ONE-TIME ENZYME TREATMENT ON PARAMECIUM

Cultures of *Paramecium tetraurelia* (obtained from American Type Culture Collection) were inoculated into tubes containing 2% DNase in protozoan broth (a 2% solution contained 4 ul of the DNase stock solution with magnesium chloride and Tris buffer, prepared as described in Example 1, added to 200 ul of protozoan broth, as well as an additional 2 ul each of I M magnesium chloride and 1M Tris buffer). The protozoan broth was prepared by adding 3 protozoa pellets to 1200 ml distilled water, boiling the solution, filtering through Whatman #1 filter paper, and autoclaving, followed by inoculation with cultures of bacteria which the paramecium cells eat, isolated from the paramecium solution obtained from the ATCC. All cell cultures were allowed to grow at room temperature.

The paramecium cells treated with 2% DNase died almost immediately. Several lower concentrations of enzyme were tested, and 1% or lower DNase was found to be suitable for testing purposes. Higher concentrations of RNase could be tolerated by the cells.

Paramecium cells were treated with 0.5% DNase or 0.5% albumin solution (in protozoan broth with salts, buffers, and bacteria as described above). After 1 week, 30 cells were isolated from each tube. Each cell was placed in a separate tube containing 0.2 ml growth medium. After 24 hours, the number of paramecium cells in each tube was counted and recorded. The mean number of DNase-treated paramecium cells was slightly higher than the albumin-treated cells; however, the difference was not statistically significant.

Paramecium cells were treated in a similar manner with 8% RNase or 8% albumin. After 2 weeks, 20 cells were isolated from each tube and placed in individual tubes. After 24 hours, the cells were counted. The mean number of albumin-treated cells in each tube was 3.4, while the mean number of RNase-treated cells was 4.85. The T value was 2.07, which was significant at the 95% level. Four days later, the paramecium cells treated with 8% RNase died. They had grown much larger than the control cells.

Various other concentrations were tested for single-dose treatments using DNase, RNase, or both. Cells treated with 1% RNase showed a slight decrease in fission rate during the first 24 hours, then a slight increase in fission rate, which became statistically significant after about 2 weeks.

Because the results of these tests and several others were not as high as anticipated, a series of tests were conducted using sequential enzyme treatments, as described in the following example.

Example 5

INHIBITION OF PARAMECIUM BY SEQUENTIAL ENZYME TREATMENTS

All paramecium cell cultures were grown in protozoan broth containing salt, buffer, and bacteria, as described above. They were treated as described below and counted 24 hours after the treatments began.

TRIAL A: Cells were treated with 1% DNase. Once each hour for the next four hours, an additional 1% DNase was added.

TRIAL B: 4% RNase was added to the solution a total of 9 times, once every 30 minutes.

TRIAL C: 4% RNase was added to the solution 5 times, once every hour.

TRIAL D: Cells were treated initially with 1.5% DNase and 1% RNase. Every 30 minutes after that, 1% RNase was added, a total of 8 times.

TRIAL E: 1% DNase and 1% RNase were added to the solution 5 times, once each hour.

TRIAL F (CONTROL): Cells were grown in broth with salt, buffer, and bacteria, with no nuclease.

The number of cells at the end of the 24 hour period in all nuclease-treated trials listed above were significantly less than the number of control cells.

Example 6

STIMULATION OF PARAMECIUM BY SEQUENTIAL ENZYME TREATMENTS

TRIAL G: 0.5% DNase was added to the solution 3 times, once every 2 hours.

TRIAL H: 2% RNase was added to the solution 3 times, once every 2 hours.

TRIAL I: Cells were treated initially with 1.5% DNase and 1% RNase, then 1% RNase was added two more times, once every 2 hours.

TRIAL J: 0.5% DNase and 0.5% RNase were added to the solution 3 times, once every 2 hours.

All cells treated as described above had higher fission rates, tested after one week. The results are shown in Table 4. The increase in the fission rate was statistically significant at the 99% level in Trials G and J. Trial I was significant at the 95% level, and Trial H was significant at the 90% level.

REFERENCES

M. I. Belyaeva et al, "Effect of Nuclease from Serratia marcescens on the multiplication of *Candida tropicalis*," *Mikrobioloqiya* 46(2): 300–303 (1977); Chem. Abstr. 87:2233y Finch and Hayflick, *Handbook of Biology and Aging*: (Van Nostrand Rheinhold, 1977).

L. Hayflick, "Cell biology of aging," *Bioscience* 25: 629–637 (1975)

Holehan and Merry, *Biol. Rev.* 61: 329–368 (1986)

F. G. Kupriyanova et al, "Stimulation of the proliferation of the yeast *Candida tropicalis* by exogenous nucleases," *Biol. Nauki (Moscow)* 10: 91–95 (1982); Chem. Abstr. 98:2639n.

A. L. Lehninger, *Biochemistry*, Second edition, Worth Publ., New York (1975)

Benjamin Lewin, *Genes*, Second edition, Wiley and Sons, New York (1985)

Masoro, *J. Nutrition* 115: 842–848 (1985)

McCay et al, *J. Nutrition* 10: 63–80 (1935)

D. M. Ogrydziak and R. K. Mortimer, "Genetics of Extracellular Protease Production in Saccharomycopsis Lipolytica," *Genetics* 87: 621–632 (1977)

D. Ogrydziak et al, *Molec. Gen. Genet.* 163: 229 t1978).

S. R. Rodermel et al, "Age-correlated changes ..." *Genetics* 87: 259–274 (1977)

T. Sano et al, "A viroid-like RNA Isolated from Grapevine has High Sequence Homology with Hop Stunt Viroid," *J. General Virology* 66: 333–338 (1985)

L. Stryer, *Biochemistry*, 2nd edition, Freeman and Co., San Francisco, Calif. (1981)

S. Tobe et al, "Production ... of *Candida Lipolytica*," *Agric. Biol. Chem.* 40: 1087–1092 (1976)

C. M. Woolf, *Statistics for Biologists: Principles of Biometry* (Van Nostrand, Princeton N.J., 1968)

D. Yarrow, *J. Microbiol. Serol.* 38: 357 (1972)

I claim:

1. A method of treating cells so as to alter phenotypic expression in the cells in an inheritable manner, wherein said cells are selected from the group consisting of Candida cells and Paramecium cells, comprising the steps of:

(a) contacting the cells with an amount of exogenous nuclease equal to about 0.5% per volume of liquid culture for a period of time equal to about two hours (b) culturing the cells for at least three generations to allow inheritable phenotypic traits to be expressed by progeny cells; and, (c) selecting progeny cells having one or more desired phenotypic traits which have been altered compared to corresponding traits of the cells before said treatment.

2. The method of claim 1 wherein the Candida cells are *Candida lipolytica*.

3. The method of claim 1 wherein the Paramecium cells are selected from the group consisting of *Paramecium aurelia*, *Paramecium caudatum* and *Paramecium tetraurelia*.

* * * * *